(12) United States Patent
Aliakbari (10) Patent No.: US 12,364,457 B2
(45) Date of Patent: Jul. 22, 2025

(54) ULTRASOUND PROBE WITH THERMAL MANAGEMENT

(71) Applicant: FUJIFILM SONOSITE, INC., Bothell, WA (US)

(72) Inventor: Saeed Aliakbari, Snohomish, WA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 114 days.

(21) Appl. No.: 18/125,575

(22) Filed: Mar. 23, 2023

(65) Prior Publication Data

US 2024/0315667 A1    Sep. 26, 2024

(51) Int. Cl.
*A61B 8/00* (2006.01)

(52) U.S. Cl.
CPC .......... *A61B 8/4472* (2013.01); *A61B 8/4422* (2013.01); *A61B 8/4455* (2013.01); *A61B 8/461* (2013.01); *A61B 8/56* (2013.01)

(58) Field of Classification Search
CPC ... A61B 8/4472; A61B 8/4422; A61B 8/4455; A61B 8/461; A61B 8/56
See application file for complete search history.

(56) References Cited

U.S. PATENT DOCUMENTS

| | | | |
|---|---|---|---|
| 2007/0234807 A1* | 10/2007 | Moore | G01H 3/12 600/437 |
| 2008/0194964 A1* | 8/2008 | Randall | A61B 8/4411 600/459 |
| 2018/0317883 A1* | 11/2018 | Huhtamaki | G01S 7/52079 |

OTHER PUBLICATIONS

Jin et al (WO 2017131280) machine translation (Year: 2017).*
Wang et al (WO 2015153033) machine translation (Year: 2015).*

* cited by examiner

*Primary Examiner* — Alexei Bykhovski
(74) *Attorney, Agent, or Firm* — Womble Bond Dickinson (US) LLP (57) ABSTRACT

An ultrasound probe with thermal management and methods for using and manufacturing the same are described. In some embodiments, an ultrasound probe includes electronics configured to control transmission and reception of ultrasound signals and a battery configured to provide power to the electronics. The ultrasound probe also includes a battery holder configured to house the battery and transfer heat away from the electronics and an enclosure configured to establish a seal that isolates the electronics from the battery and an environment external to the ultrasound probe.

19 Claims, 10 Drawing Sheets

ULTRASOUND PROBE WITH THERMAL MANAGEMENT

FIELD

Embodiments disclosed herein relate to ultrasound systems. More specifically, embodiments disclosed herein relate to ultrasound probes having batteries and using thermal management.

BACKGROUND

Ultrasound systems can generate ultrasound images by transmitting sound waves at frequencies above the audible spectrum into a body, receiving echo signals caused by the sound waves reflecting from internal body parts, and converting the echo signals into electrical signals for image generation. To generate and receive the ultrasound signals, ultrasound systems include transducer arrays that are usually included in a handheld probe. Because the transmission and reception of the ultrasound signals involve electronic circuitry that can consume significant amounts of power, the ultrasound probes can generate significant amounts of heat. Failure to manage the thermal properties of the ultrasound probe can directly affect the usability of the ultrasound system by (i) reducing scan time, (ii) increasing periods between scans, and (iii) causing discomfort to the patient and operator. Consequently, ultrasound probes usually include some form of heat dissipation.

For instance, wired ultrasound probes (e.g., probes that are connected to an ultrasound machine via one or more wires/cables) often include internal heat management devices. However, these heat management devices are generally not applicable to wireless ultrasound probes (e.g., probes that are coupled to an ultrasound machine via a wireless communication link) because they introduce obstacles for the internal battery required in wireless ultrasound probes. For instance, the heat management devices can take up room in the probe and prevent the insertion of a battery in the probe, or limit the size, and hence capacity, of the battery. Moreover, conventional ultrasound probes with a modified external surface to manage heat, such as fins, ridges, grooves, etc., introduce difficulties for cleaning the probe and result in areas for contaminants to collect.

Furthermore, wireless ultrasound probes usually include electronics not found in wired ultrasound probes, such as transceiver chips to connect to the wireless communication link coupling the wireless ultrasound probe and an ultrasound machine/display device. Consequently, wireless ultrasound probes can generate more heat than wired ultrasound probes. In some cases, the heat can be significant enough to limit the functionality of the wireless probe. For instance, according to System-Level Design of an Integrated Receiver Front End for a Wireless Ultrasound Probe, di Ianni, T., et al., (2016), IEEE Transactions on Ultrasonics, Ferroelectrics and Frequency Control, 63(11), pp. 1935-1946, the limit on power consumption of a wireless ultrasound probe is approximately 3 watts when the thermal strategy is to spread the heat uniformly. Accordingly, the utility of wireless ultrasound probes may not be fully realized because of the heat generated by these probes.

SUMMARY

An ultrasound probe with thermal management and methods for using and manufacturing the same are described. In some embodiments, an ultrasound probe includes electronics configured to control transmission and reception of ultrasound signals and a battery configured to provide power to the electronics. The ultrasound probe also includes a battery holder configured to house the battery and transfer heat away from the electronics and an enclosure configured to establish a seal that isolates the electronics from the battery and an environment external to the ultrasound probe.

In some embodiments, an ultrasound system includes a display device configured to display ultrasound images based on ultrasound data and an ultrasound probe communicatively coupled to the display device and configured to generate the ultrasound data. In some embodiments, the ultrasound probe includes electronics housed in a first compartment of the ultrasound probe and configured to control the generation of the ultrasound data and a battery housed in a second compartment of the ultrasound probe and configured to provide power to the electronics. In some embodiments, the ultrasound probe also includes a probe cover and a battery holder that when attached to the probe cover forms a seal that isolates the first compartment from the second compartment.

In some embodiments, a method of manufacturing an ultrasound probe includes forming a battery holder configured to house a battery in a first compartment of the battery holder, mounting electronics to the battery holder outside of the first compartment, and sealing a probe cover to the battery holder, the sealing creating a second compartment inside the ultrasound probe that houses the electronics and that is isolated from the first compartment and an environment external to the ultrasound probe.

Other systems, machines and methods for an ultrasound probe with thermal management are also described.

BRIEF DESCRIPTION OF THE DRAWINGS

The appended drawings illustrate examples and are, therefore, exemplary embodiments and not considered to be limiting in scope.

DETAILED DESCRIPTION

In the following description, numerous details are set forth to provide a more thorough explanation of the embodiments described herein. It will be apparent, however, to one skilled in the art, that the embodiments may be practiced without these specific details. In other instances, well-known structures and devices are shown in block diagram form, rather than in detail, in order to avoid obscuring the present invention.

Systems, devices, and techniques are disclosed herein that include a battery holder internal to an ultrasound probe that (i) pulls heat away from the battery, electronics, and probe surface, and towards the distal end of the probe, (thus away from the user's hand and away from the lens), (ii) seals the internal electronics of the probe from the battery, and (iii) allows the battery to be serviced without breaking the seal. The use of these techniques overcomes the limitations in the usefulness of conventional ultrasound probes, including wireless ultrasound probes, because of the heat generated by these probes, as well as wired ultrasound probes. Note that the terms "probe" and "scanner" are used herein to mean the same thing.

Figure 1:
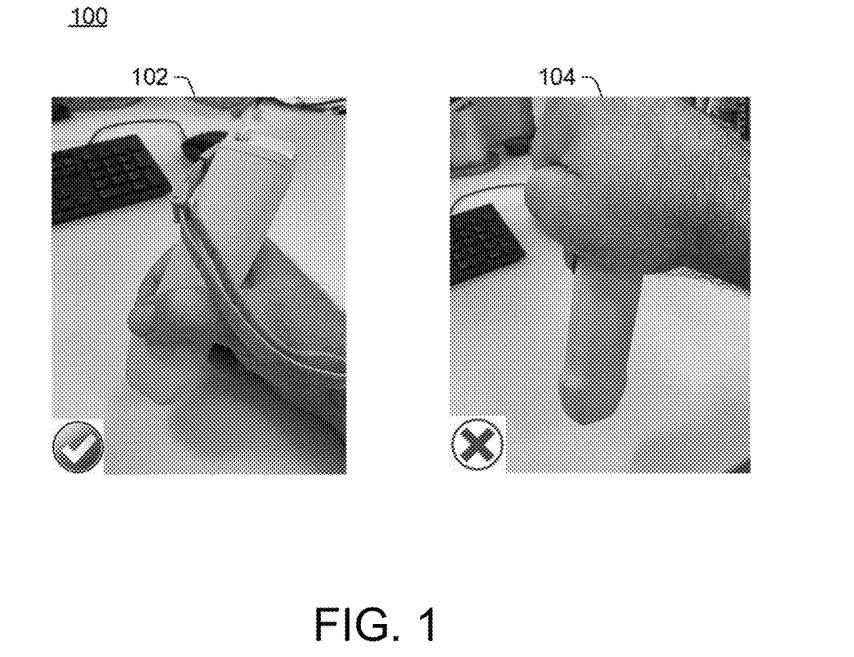
FIG. 1 illustrates an operator holding a wireless ultrasound probe.

FIG. 1 depicts generally at 100 two images 102 and 104 of a user holding a wireless ultrasound probe. In image 102, the user holds the wireless ultrasound probe so that the distal end (i.e., the end of the probe with the lanyard attached in FIG. 1) is not obstructed, considered by some to be the usual way that a user holds the ultrasound probe. In contrast, image 104 depicts an unorthodox grip orientation in which the user is holding the wireless ultrasound probe in such a way as to cover the distal end of the probe, considered by some to be a grip orientation almost never used by sonographers. For example, most wired ultrasound probes include a cable that extends from the distal end of the ultrasound probe, prohibiting the grip orientation depicted in image 104. Since most operators grip wireless ultrasound probes in a similar way to how they grip wired ultrasound probes, the operator does not usually (if ever) cover the distal end of the ultrasound probe with their hand. Hence, as discussed herein, the ultrasound probes include heat management devices that direct heat towards the distal end of the probe, away from the lens that is facing the patient and away from the probe surface where the operator usually grips the probe.

Figure 2A:
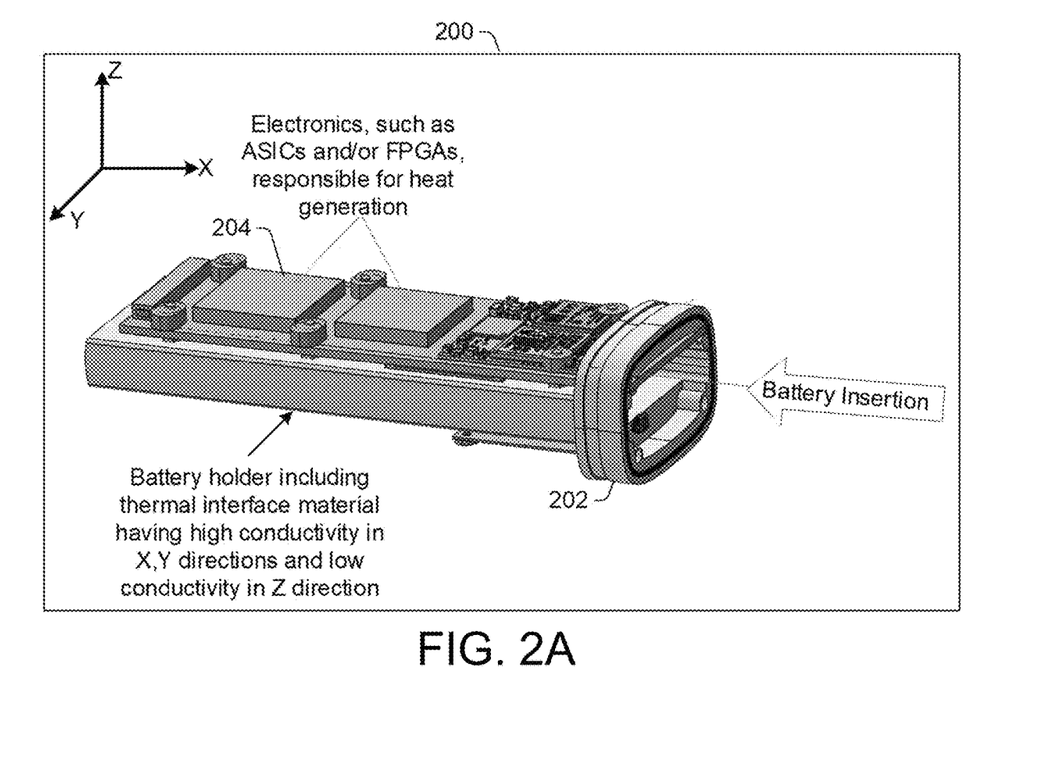
FIG. 2A depicts generally a battery holder for an ultrasound probe in accordance with some embodiments.

FIG. 2A depicts generally at 200 a battery holder 202 for an ultrasound probe in accordance with some embodiments. The battery holder 202 can be implemented as an internal part of an ultrasound probe, and can house a battery in any suitable portion of the battery holder 202, such as inside the battery holder 202 so that the battery is at least partially enclosed by the battery holder 202 (described below in more detail with respect to FIG. 2C). Note that the battery is not shown in FIG. 2A for clarity, but the arrow in FIG. 2A indicates the direction of battery insertion into the battery holder 202.

The battery holder 202 can house a battery in any suitable portion of the battery holder 202. In some embodiments, the ultrasound probe includes the battery that is placed inside a central portion of the battery holder. In some embodiments, the battery can be inserted so that it sits in a bottom or top portion of the battery holder 202, rather than sandwiched in the middle of the battery holder 202. For instance, the battery can be inserted through and in the middle of the battery holder 202, and then be dropped or moved to one side. In an example, the battery when inside the battery holder 202 can be covered with a lid. In some embodiments, the lid is flexible because the battery can swell by up to 10% in size when charging.

The battery holder 202 can be implemented as a multi-functional part of the ultrasound probe. For example, as illustrated in FIG. 2A, the battery holder 202 serves as a mount to hold electronics 204. Additionally, the battery holder 202 serves as a heat sink to direct heat away from the electronics 204 and towards the distal end of the ultrasound probe. The electronics 204 can include any suitable electronics for operation of the ultrasound probe, including amplifiers and drive circuitry to generate and receive ultrasound signals, beamforming circuits, power control circuits (e.g., to dynamically control the power consumption of the ultrasound probe), one or more transceivers to implement a wireless communication link, a digital signal processor (e.g., a programmable processing unit, graphics processor, etc.), and the like. In some embodiments, the electronics 204 include integrated circuits, such as ASICs and/or FPGAs.

The battery holder 202 can be mounted to the electronics 204 in any suitable way. In an example, the electronics 204 are mounted on a printed circuit board (PCB), and the PCB is mounted to the battery holder 202. In some embodiments, the PCB is oriented so that at least some of the electronics 204 are in thermal contact with the battery holder 202. For instance, the integrated circuits of the electronics 204 are depicted in FIG. 2A so that they are visible for clarity. However, the PCB that the integrated circuits are mounted on can be flipped so that the integrated circuits, or at least a portion of them, are on the bottom of the PCB and in contact with the battery holder 202. Additionally or alternatively, the integrated circuits can be mounted on the bottom of the PCB and in contact with the battery holder 202. The electronics 204 can be a significant source for heat generation in the ultrasound probe. By mounting the electronics 204 so that they are in contact with the battery holder 202, the battery holder 202 can better transfer heat away from the electronics 204 and towards the distal end of the probe.

To direct heat towards the distal end of the probe, the battery holder 202 can be made of a material having different thermal properties in different directions. That is, the battery holder 202 can have material having different thermal properties in different directions installed on it, or embedded in it. For instance, with respect to the coordinate system illustrated in FIG. 2A, the battery holder 202 can be made of a thermal interface material having high thermal conductivity in X and Y directions, and low thermal conductivity in the Z direction. Accordingly, the battery holder 202 can direct heat away from the surface of the probe where a user usually grips the probe, away from the electronics 204, and towards the distal end of the probe.

To accomplish this thermal directivity, the thermal interface material of the battery holder 202 can be doped with micro-materials, such as micro-fibers, micro-pipes, micro-rods, etc., that are aligned in the thermal interface material to enhance heat flow in X and Y directions and inhibit heat flow in the Z direction. The thermal interface material and/or the micro-materials can be made of magnesium, aluminum, resin, combinations thereof, and the like.

In some embodiments, the thickness of the battery holder 202 varies. For instance, the thickness of the battery holder 202 can be greater (e.g., up to ten times the thickness) where the electronics 204 are located compared to where the electronics 204 are not located. This added thickness can further help pull heat away from the electronics 204, through the battery holder 202, and towards the distal end of the probe. In an example, the battery holder 202 can act as a shield against noise. For instance, the walls (sides) of the battery holder 202 can be increased in height (e.g., in the Z direction) relative to what is depicted in FIG. 2A to shield the electronics 204 and reduce/prevent undesired emissions, such as electromagnetic interference that could otherwise leak onto the transducer array, traces on the printed circuit board (PCB), etc.

Figure 2B:
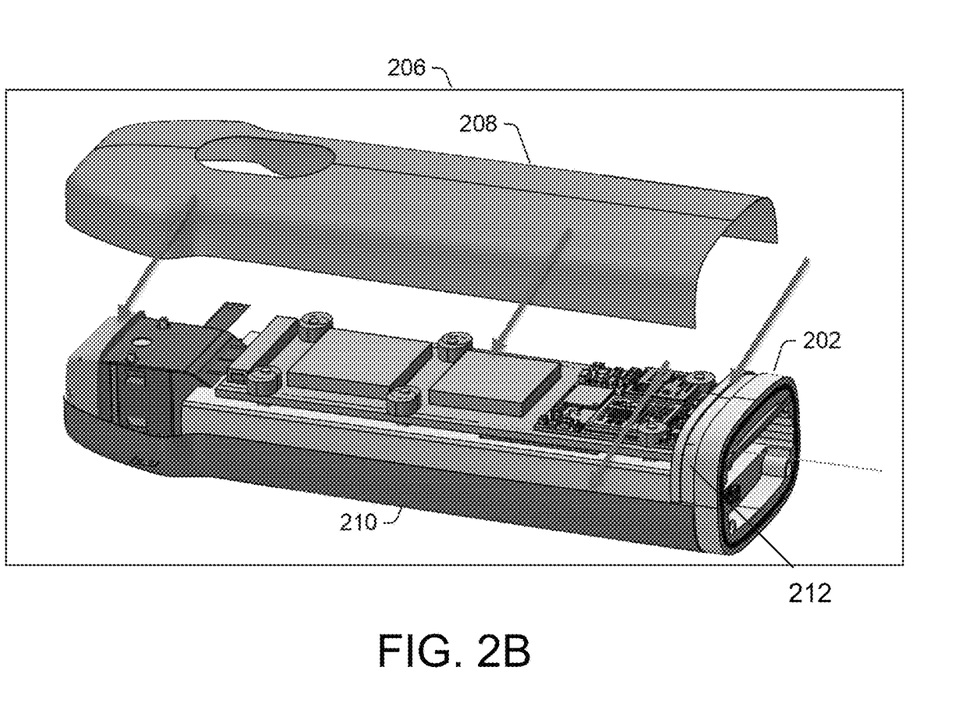
FIG. 2B illustrates generally an assembly of an ultrasound probe in accordance with some embodiments.

FIG. 2B illustrates generally at 206 the assembly of an ultrasound probe in accordance with some embodiments. The battery holder 202 is integrated with transducer electronics (e.g., a transducer array) at the proximal end of the probe (e.g., the opposite end of the probe from the distal end), and the assembly is enclosed by an upper cover 208 and a lower cover 210. The covers 208 and 210 can be mechanically attached such as with external fasteners, shapes formed (e.g., molded or milled) into the two covers so that when they are joined together, they are "locked" with respect to one another, and the like.

Furthermore, the assembly of the two covers 208 and 210 around the battery holder 202 forms a seal so that the electronics 204 are sealed from the environment outside the probe and also from the internal compartment of the battery holder 202 where the battery is placed. In some embodiments, the seal is IPX7 rated. To form this seal, a bonding agent, such as silicone, e.g., room-temperature-vulcanizing (RTV) silicone, can be placed along the mating edges of the covers 208 and 210, and along the edges of the battery holder 202 that mate with the covers 208 and 210, as indicated by the arrows in FIG. 2B. As illustrated in FIG. 2B, the battery holder 202 can include a groove 212 to hold the silicone and mate with the covers 208 and 210 at the distal end of the probe.

Since the covers 208 and 210 can be assembled with the battery holder 202 without the battery being yet placed in the battery holder 202, this assembly process allows the silicone to be oven cured without the battery present in the probe, so the battery is not harmed by the heat. In contrast, some conventional ultrasound probes with internal batteries usually include the battery when silicone is oven cured. To prevent damage to the battery, the assembly process for the conventional ultrasound probes either reduces the heat, which can result in a poor seal, or risks damaging the battery because of excessive heat.

Figure 2C:
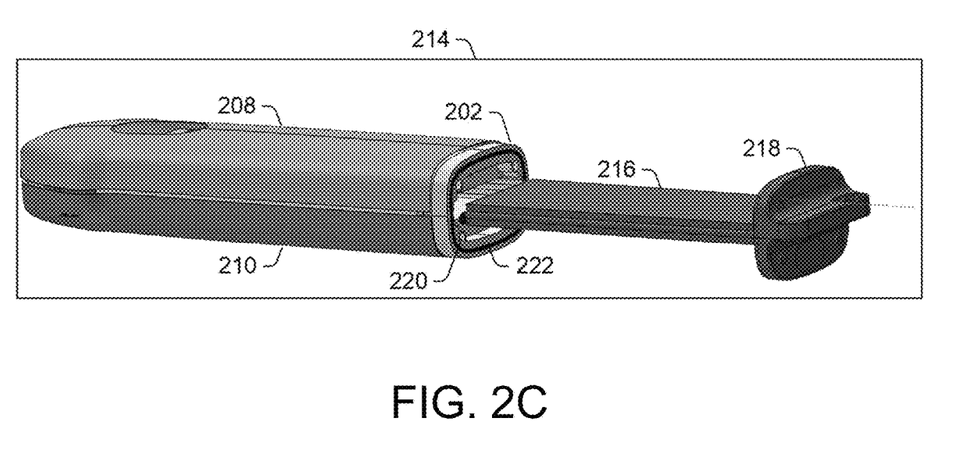
FIG. 2C depicts generally an assembled ultrasound probe and a battery being inserted in accordance with some embodiments.

FIG. 2C depicts generally at 214 an assembled ultrasound probe and battery 216 being inserted in accordance with some embodiments. The battery 216, attached to an end cap 218, can be slid into the battery holder 202 that is assembled with the covers 208 and 210. To seal the battery 216 from the environment outside the probe, the end cap 218 is attached to holes 220 of the battery holder 202, and an O-ring 222 is sandwiched between the end cap 218 and the distal end of the battery holder 202. The holes 220 can be drilled and tapped with threads that mate with fasteners (e.g., bolts) placed through corresponding thru holes on the end cap 218. When tightened to a proper torque, the fasteners squeeze the end cap 218 against one side of the O-ring 222, and the other side of the O-ring 222 against the battery holder 202.

Figure 2D:
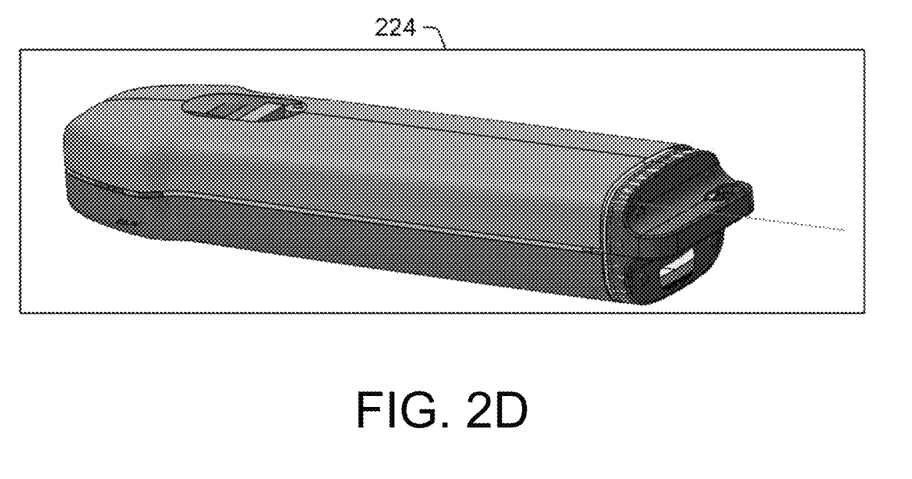
FIG. 2D depicts an assembled ultrasound probe in accordance with some embodiments.

FIG. 2D depicts at 224 an assembled ultrasound probe in accordance with some embodiments. The internals of the probe, including the electronics 204, are completely sealed from the battery 216, and the probe itself is sealed from the environment outside the probe. In an example, the probe is sealed with at least an IPX7 rating. In an example, the battery is inserted into the probe at the time of shipment to preserve battery life/capacity, compared to storing the probe prior to shipment with the battery inserted.

In some embodiments, the ultrasound probe constitutes numerous advantages over conventional ultrasound probes. From a thermal perspective, the design of the ultrasound probe pulls heat away from the electronics, battery, lens, and probe surface (e.g., grip surface). This heat management results in longer scan times and shorter waits between scans compared to conventional ultrasound probes, which improves the patient experience and allows the sonographer to more efficiently use their time. Moreover, the heat management of the ultrasound probe results in less discomfort to both the operator and the patient, compared to conventional ultrasound probes.

Furthermore, the ultrasound probe of some embodiments can tolerate higher temperatures than conventional ultrasound probes because heat is not spread uniformly. Hence, a wireless ultrasound probe of some embodiments is not limited to the approximate 3-watt power consumption as described in System-Level Design of an Integrated Receiver Front End for a Wireless Ultrasound Probe, di Ianni, T., et al., (2016), IEEE Transactions on Ultrasonics, Ferroelectrics and Frequency Control, 63(11), pp. 1935-1946. Accordingly, the wireless ultrasound probe can support additional functionalities compared to conventional wireless ultrasound probes. An example of an additional functionality includes the integration of multiple Wi-Fi transceivers in the wireless ultrasound probe, so that it can communicate simultaneously with a display device and an access point of a care facility, as described, for example, in U.S. patent application Ser. No. 17/830,066, entitled "Ultrasound Scanner that Supports Handset Wireless Network Connectivity," filed Jun. 1, 2022, incorporated herein by reference.

From a seal perspective, the ultrasound probe of some embodiments seals the internal electronics of the probe from the battery. Hence, if a battery fails, such as due to leaking, it will not contaminate the electronics of the probe. As a result, an ultrasound probe can remain in service by simply replacing the battery, rather than forcing the care facility to replace the probe or send it out for repair. Hence, the care facility can save costs while maintaining better patient care, compared to the use of conventional ultrasound probes that require repair or replacement when a battery fails. Moreover, the battery of the ultrasound probe of some embodiments can be serviced (e.g., replaced) while maintaining the IPX7 rated seal, which is simply not possible for a conventional ultrasound probe that requires the probe to be unsealed for battery service.

From a structural perspective, the ultrasound probe of some embodiments includes a multi-purpose structure (e.g., the battery holder 202) that supports and mounts an electronics assembly, isolates and houses a battery, directionally transfers heat, and shields the probe from noise emitted from the electronics. Moreover, the battery can be serviced without damaging the electronics or the transducer array.

Furthermore, in some embodiments, the surface of the ultrasound probe does not require complex features for thermal dissipation, such as ridges, fins, grooves, and the like. Hence, the ultrasound probe affords simple and superior cleaning procedures, decreasing probability of contamination compared to conventional ultrasound probes with complex surface features for cooling. In one example, an ultrasound system includes an ultrasound probe of some embodiments as previously described, and a cooling system. The cooling system can include a liquid filled pod (e.g., a container filled with a cooling agent, such as water), in which the ultrasound probe can be completely submerged for cooling. In some embodiments, the probe can be submerged when powered on or off, because of the IPX7 seal.

Figure 3:
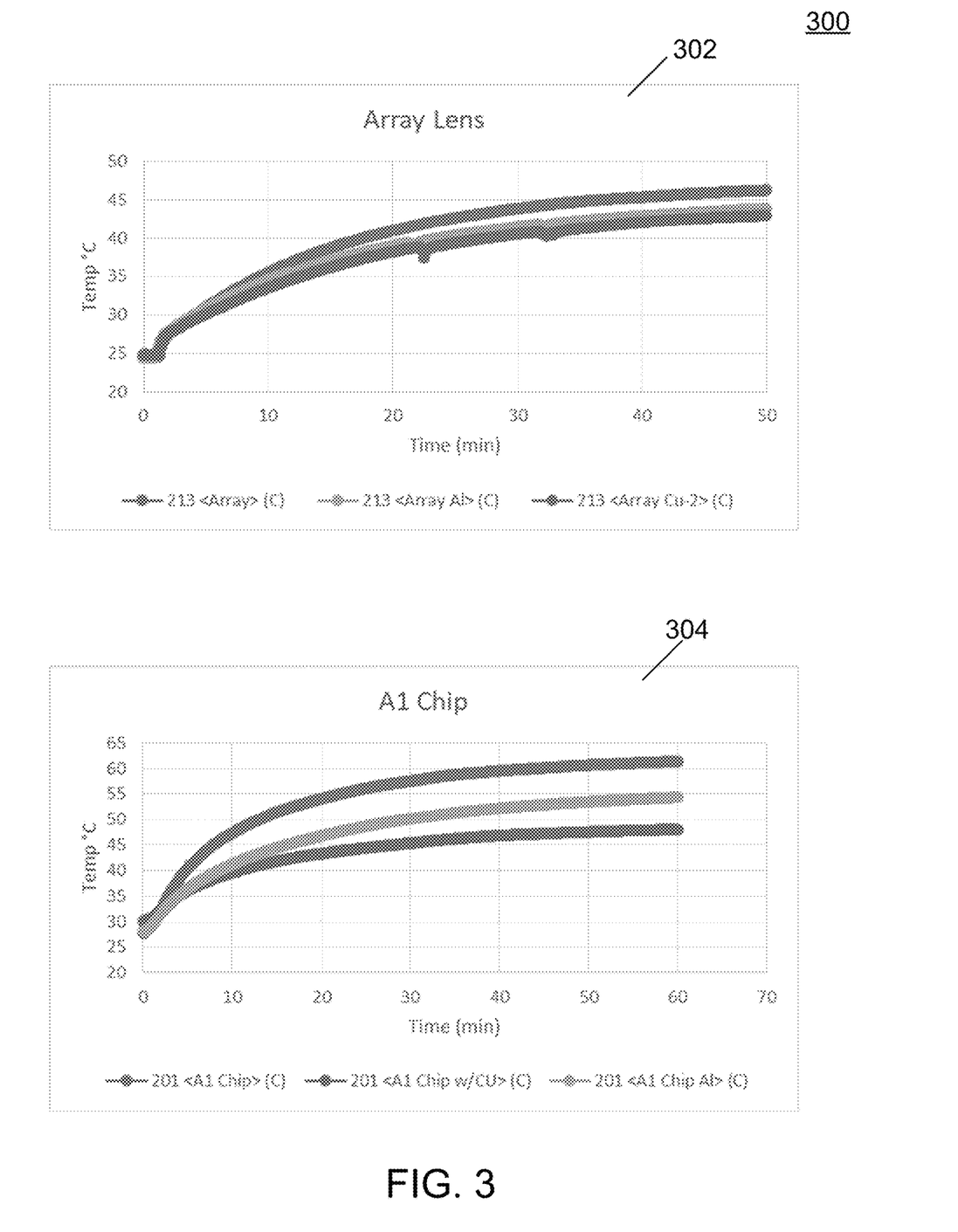
FIG. 3 depicts thermal results for various components of an ultrasound probe in accordance with some embodiments.

FIG. 3 depicts at 300 thermal results for various components of an ultrasound probe, including the transducer lens (e.g., at the proximal end of the probe) at 302, an ASIC (e.g., a component of electronics 204) at 304, a battery (e.g., battery 216) at 306, and an end cap (e.g., end cap 218) at

308. The thermal results are gathered for two probes. A first probe is a conventional ultrasound probe that does not include a battery holder that transfers heat (e.g., battery holder 302) as described above. These results are labeled as "baseline". A second probe is an ultrasound probe according to some embodiments and includes a battery holder made of copper for heat transfer that is similar to the battery holder 302 described above. These results are labeled as "copper". The tests are conducted for 40° C., with scan times of 6.5 minutes for the baseline results and 10.2 minutes for the copper results. The temperature of 40° C. is selected because it is the maximum operating ambient environment temperature for many ultrasound products. At 302, the temperature profiles for the lens are depicted, and there is little difference between the two ultrasound probes. However, at 304, the temperature profiles for the ASIC are shown, and the ultrasound probe of some embodiments keeps the ASIC cooler for longer and with a less peak temperature, compared to the conventional ultrasound probe. At 306, the temperature profiles for the battery show similar rise times for both probes, with a higher peak temperature for the ultrasound probe of some embodiments, due to the longer scan time of 10.2 minutes compared to 6.5 minutes for the conventional ultrasound probe. At 308, the temperature profiles for the end cap are shown, which emphasizes the utility of the invention, as the heat is pulled to the end cap for the ultrasound probe of some embodiments.

Base Station and Charging Station

Figure 4:
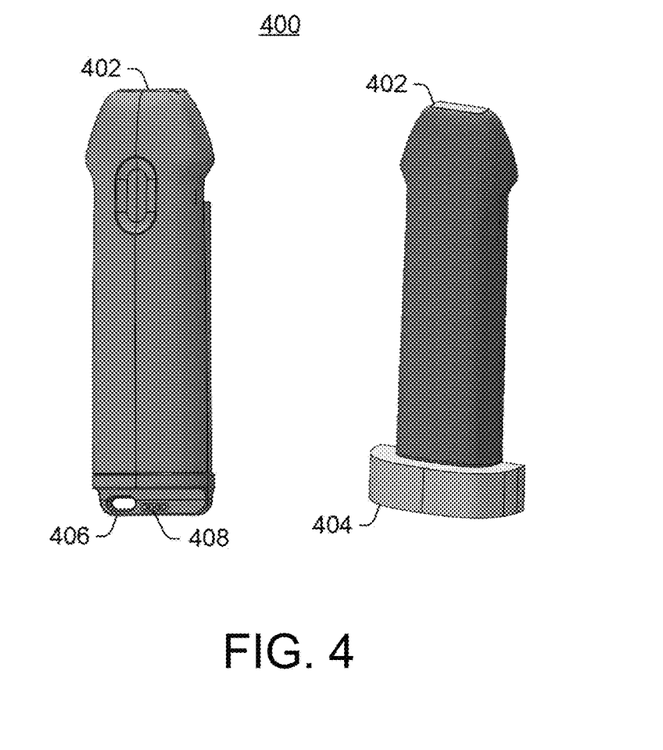
FIG. 4 depicts an ultrasound probe and a portable base station in accordance with some embodiments.

In an example, an ultrasound system includes an ultrasound probe as described above, and a portable base station that can be attached to the probe (e.g., to the end cap of the probe) to instantly increase battery capacity and scan time, and further provide a mechanism to draw heat away from the patient, the probe electronics, and the surface of the probe where the operator grips the probe. FIG. 4 depicts generally at 400 an ultrasound probe 402 and portable base station 404. The ultrasound probe 402 is an example of the ultrasound probe previously described in FIGS. 2A-2D. As depicted in the left side of FIG. 4, the ultrasound probe 402 includes an end cap 406, which is an example of the end cap 218 as previously described. The end cap 406 includes a connector 408 that can include any number of electrical contacts for connecting the ultrasound probe 402 to the portable base station 404 (as is depicted in the right side of FIG. 4), while still maintaining the IPX7 rated seal for the ultrasound probe 402. In some embodiments, connector 408 can connect to a cable as well, so that the connector 408 attaches to the portable based station 404 and to a cable. The dual capability allows the ultrasound probe 402 to operate in either wirelessly or with a wire. In some embodiments, in such a case, when cable is connected, the load is sensed and transceiver of the probe is disabled.

The base station 404 includes a battery that can be charged via a cable (not shown in FIG. 4), wirelessly via induction, etc. When the base station 404 is connected to the ultrasound probe 402, the ultrasound probe 402 can switch from using a battery internal to the ultrasound probe 402 (e.g., the battery 216 as previously described), and the battery included in the base station 404. In some embodiments, the battery included in the base station 404 can be implemented to charge the battery internal to the ultrasound probe 402.

By attaching the base station 404 to the ultrasound probe 402, the scan time of the ultrasound probe 402 is immediately increased. For example, if the battery internal to the ultrasound probe 402 and the battery of the base station 404 have the same capacity, then the scan time is effectively doubled compared to using the ultrasound probe 402 without the base station 404. In some embodiments, the base station 404 can be connected via a cable to an AC outlet (e.g., 110 Volts, 60 Hz). In this case, the ultrasound probe 402 in combination with the base station 404 can be used for continuous scanning. In some embodiments, one or both of the batteries can be charged while the base station 404 is connected to an AC outlet.

In some embodiments, the base station 404 is made at least in part of a material having different thermal properties in different directions, as previously described with respect to the battery holder 202. For instance, the base station 404 can be made of a thermal interface material having high thermal conductivity in X and Y directions, and low thermal conductivity in the Z direction. Accordingly, the base station 404 can work in conjunction with the battery holder 202 and pull heat away from the end cap and probe. Thus, by using the base station 404, scan times can be increased not only because of the additional battery capacity, but also due to the improved thermal management that removes heat from the probe, patient, and operator.

Figure 5:
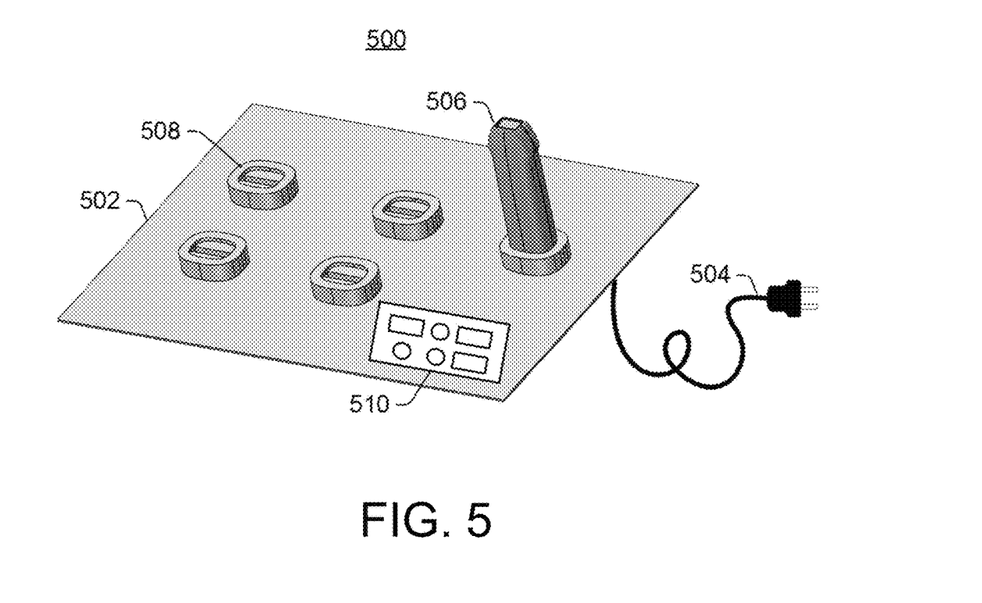
FIG. 5 illustrates generally an ultrasound charging station.

In some embodiments, the ultrasound system includes a charging mechanism for housing and charging the base stations (e.g., the base station 404). FIG. 5 illustrates generally at 500 an ultrasound charging station 502. The charging station 502 can be implemented in any suitable form factor, such as a charging mat that can be attached to an ultrasound machine. The charging station 502 includes a power cord 504 to provide power (e.g., from an AC source, such as a wall outlet) to charge a battery of an ultrasound probe 506 and/or a battery of a base station 508. In FIG. 5, the ultrasound probe 506 is an example of an ultrasound probe described above with respect to FIGS. 2A-2D, and the base station 508 is an example of the base station 404 described in FIG. 4.

The charging station 502 also includes indicators and controls 510, which can display any suitable status of the charging station 502, the ultrasound probe 506, and/or the base station 508. For instance, the indicators and controls 510 can indicate that a device (e.g., the base station 508) is connected to the charging station 502, a status of a battery of the base station 508, a status of a battery of the ultrasound probe 506, etc. Moreover, the indicators and controls 510 can provide a control option for controlling any suitable parameter of the charging station 502, the ultrasound probe 506, and/or the base station 508. Examples of parameters controllable by indicators and controls 510 include selection of a charging profile (e.g., an amount of current applied over a time period, a charging time, a fast charge mode, etc.).

Manufacturing Some Embodiments of the Ultrasound Probe

To manufacture an ultrasound probe in accordance with some embodiments, a battery holder configured to house a battery in a first compartment of the battery holder is formed. Forming the battery holder can include milling, casting, 3D printing, cutting, etc. the battery holder.

Electronics are mounted to the battery holder outside of the first compartment. Mounting the electronics can include placing the electronics on a printed circuit board and attaching the printed circuit board to the battery holder. Additionally or alternatively, mounting the electronics can include bonding a circuit, such as an integrated circuit or chip of the electronics, to the battery holder.

The above assembly 'engine' can be tested to ensure all PCB functionality prior to attaching an ultrasound array using a flex cable. At this point, the 'ultrasound engine' is completed, and additional functional testing can be done prior to sealing the scanner assembly.

A probe cover is sealed to the battery holder. The probe cover can include two or more parts, such as an upper cover and a lower cover, that are attached to one another and are sealed to the battery holder. In one example, the probe cover is a single part whose shape can be formed as part of the sealing process. Sealing creates a second compartment inside the ultrasound probe that houses the electronics. The second compartment is isolated from the first compartment and an environment external to the ultrasound probe. A bonding agent, such as, for example, RTV silicon, can be placed between the probe cover and the battery holder, and sealing can include curing the bonding agent, such as by placing the ultrasound probe in an oven. In an example, the battery is not within the ultrasound probe when the bonding agent is cured. Hence, the temperature of the curing process can be increased without risk of damaging the battery, in contrast to the manufacture of conventional ultrasound probes. After the seal is achieved the ultrasound scanner can be safety tested, as well as AIM (Acoustic Intensity Monitoring) and line sync., which happen with the scanner dipped in water before inserting battery and sealing the rear. This testing method is an advantage over testing methods for conventional ultrasound probes, in which the testing is done with the battery installed within the probe.

The fully tested ultrasound engine can reside on a shelf until an order needs to be fulfilled. A battery can be inserted into the first compartment of the battery holder when the order is ready to ship to preserve battery life/capacity. An end cap can be attached to the battery holder to seal the first compartment and the battery from the environment external to the ultrasound probe. Attaching the end cap can include placing an O-ring between the end cap and the battery holder, such as in a groove formed into the battery holder, and tightening the end cap with one or more fasteners, such as four bolts.

Figure 6:
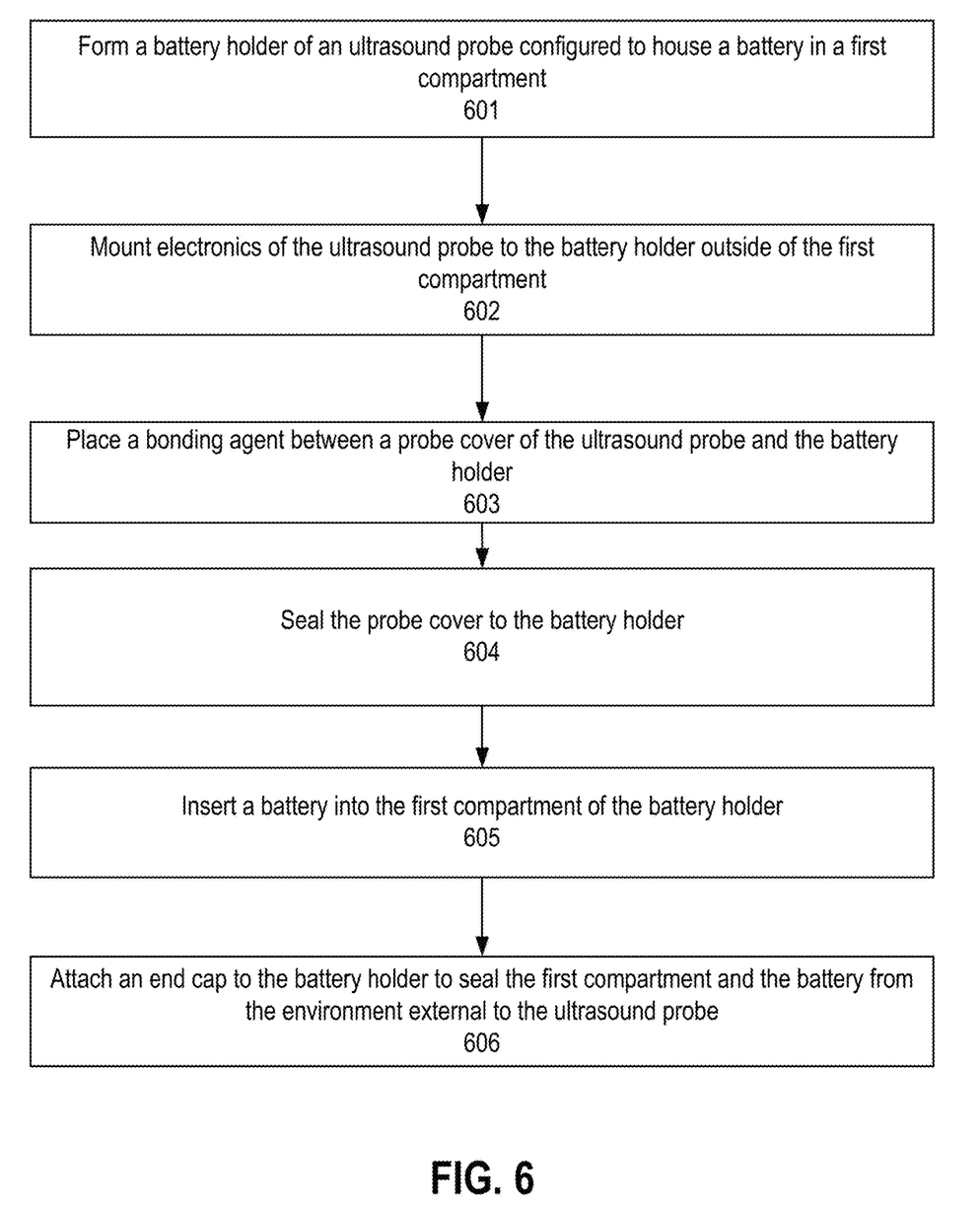
FIG. 6 is a data flow diagram of a process for manufacturing an ultrasound probe according to some embodiments.

FIG. 6 is a data flow diagram of a process 600 for manufacturing an ultrasound probe. The process is performed by processing logic that may comprise hardware (circuitry, dedicated logic, etc.), software (such as is run on a general-purpose computer system or a dedicated machine), firmware, or combinations thereof. In some embodiments, the ultrasound probe comprises one of the ultrasound probes described above in conjunction with FIGS. 1-5. In some embodiments, the process is performed by one or more processing machines.

Referring to FIG. 6, the process begins by processing logic forming a battery holder configured to house a battery in a first compartment of the battery holder (processing block 601). After forming the battery holder, processing logic mounts electronics to the battery holder outside of the first compartment (processing block 602) and places a bonding agent between a probe cover and the battery holder (processing block 603).

After placing a bonding agent between a probe cover and the battery holder, processing logic seals the probe cover to the battery holder (processing block 604). In some embodiments, processing logic seals the probe cover to the battery holder and creates a second compartment inside the ultrasound probe that houses the electronics and that is isolated from the first compartment and an environment external to the ultrasound probe. In some embodiments, sealing the probe cover to the battery holder includes curing the bonding agent with the battery removed from the ultrasound probe. Once the probe cover has been sealed to the battery holder, processing logic inserts a battery into the first compartment of the battery holder (processing block 605) and attaches an end cap to the battery holder to seal the first compartment and the battery from the environment external to the ultrasound probe (processing block 606).

Figure 7:
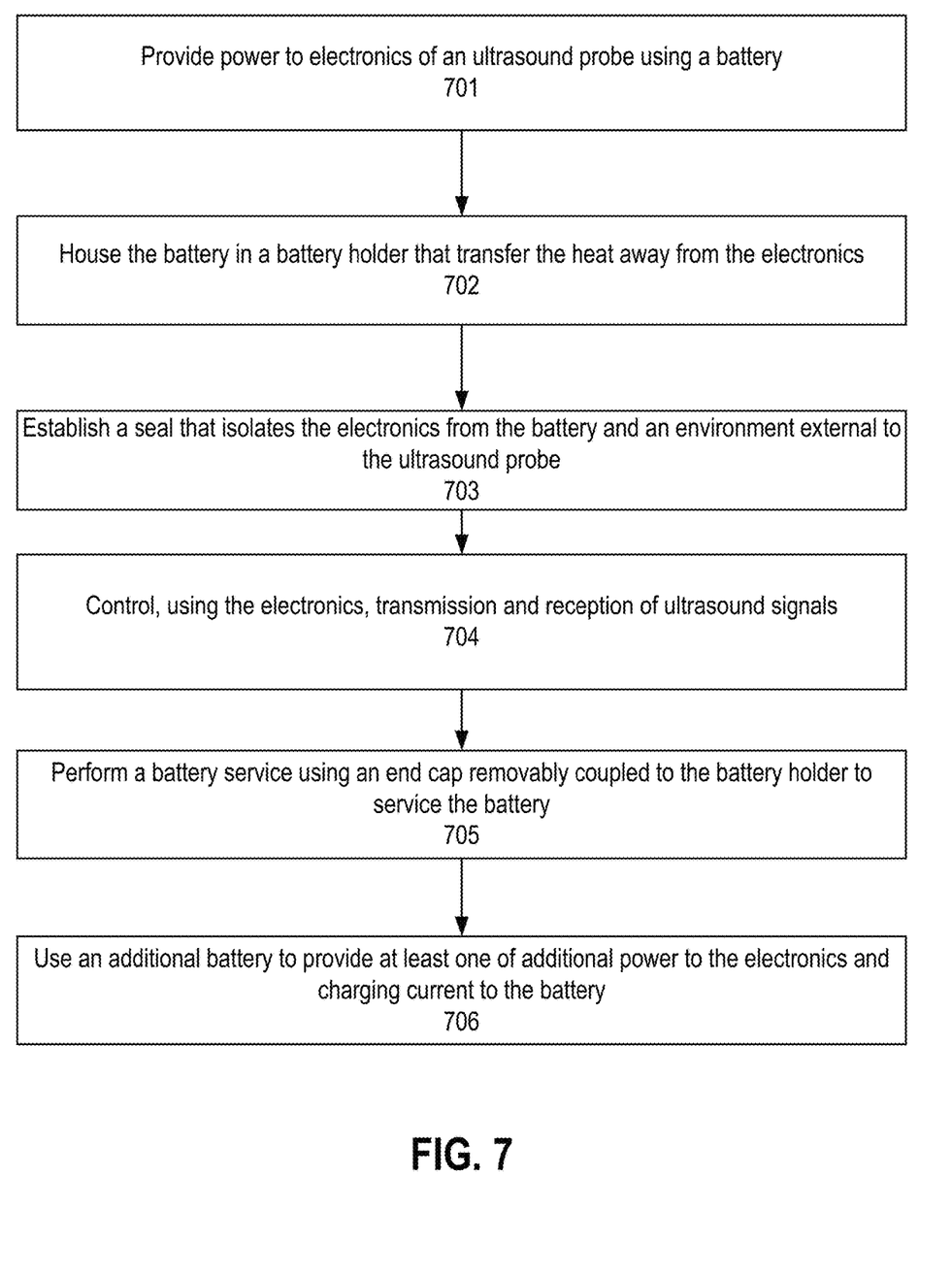
FIG. 7 is a data flow diagram of a method performed by or in conjunction with an ultrasound probe according to some embodiments.

FIG. 7 is a data flow diagram of a method 700 performed by or in conjunction with an ultrasound system having an ultrasound probe. The process is performed by processing logic that may comprise hardware (circuitry, dedicated logic, etc.), software (such as is run on a general-purpose computer system or a dedicated machine), firmware, or combinations thereof. In some embodiments, the ultrasound probe comprises one of the ultrasound probes described above in conjunction with FIGS. 1-5.

Referring to FIG. 7, the method includes providing power to electronics of an ultrasound probe using a battery (block 701) and housing the battery in a battery holder that transfers the heat away from the electronics (block 702). In some embodiments, the electronics are mounted to a printed circuit board that is attached to the battery holder.

In some embodiments, the battery holder and the enclosure are implemented to allow service of the battery without breaking the seal. In some embodiments, the battery can be serviced using a replacement battery. In some embodiments, replacing the battery I performed without opening the rest of the assembly which introduces risk in damaging the expensive lens assembly. In some embodiments, the battery holder comprises a material having a first thermal conductivity in a first direction and a second thermal conductivity in a second direction. In some embodiments, prior to shipment of the ultrasound probe the battery is stored outside the battery holder, and the battery is inserted into the battery holder for the shipment of the ultrasound probe.

The method also includes establishing a seal that isolates the electronics from the battery and an environment external to the ultrasound probe (block 703). The method further includes controlling, using the electronics, transmission and reception of ultrasound signals (block 704).

In some embodiments, the method further includes performing a battery service using an end cap removably coupled to the battery holder to service the battery (block 705). In some embodiments, the battery holder is implemented to transfer the heat away from the electronics and towards the end cap.

As part of the battery service, the method includes using an additional battery to provide at least one of additional power to the electronics and charging current to the battery (block 706). In some embodiments, the end cap includes at least one connector implemented to receive additional power and/or the charging current from the additional battery. In some embodiments, the additional battery is implemented to be removably attached to the end cap. In some embodiments, the additional battery is housed in a material having a first thermal conductivity in a first direction and a second thermal conductivity in a second direction.

Figure 8:
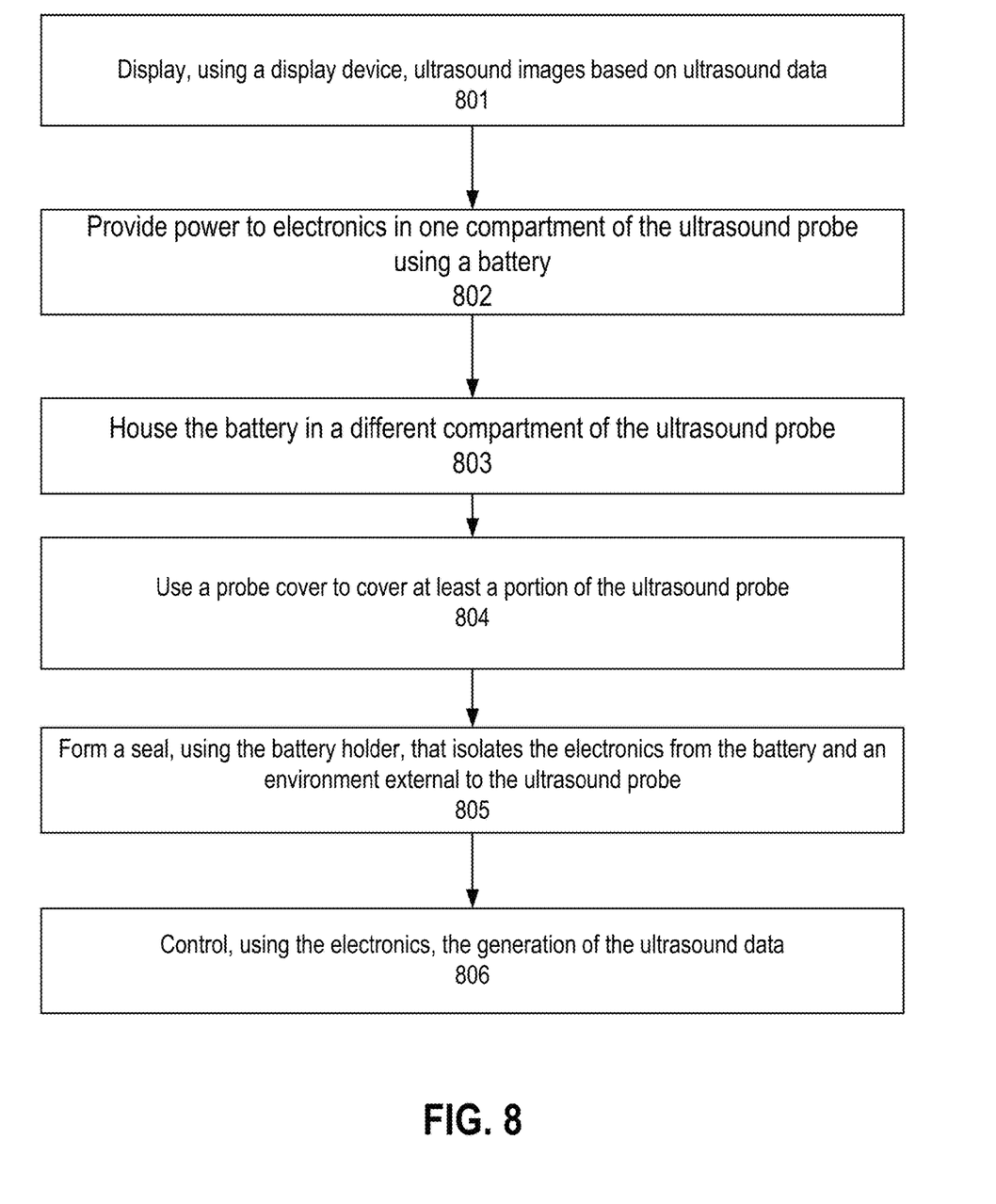
FIG. 8 is a data flow diagram of a method performed by or in conjunction with an ultrasound system having an according to some embodiments.

FIG. 8 is a data flow diagram of a method 800 performed by or in conjunction with an ultrasound system having an ultrasound probe. The process is performed by processing logic that may comprise hardware (circuitry, dedicated logic, etc.), software (such as is run on a general-purpose computer system or a dedicated machine), firmware, or combinations thereof. In some embodiments, the ultrasound probe comprises one of the ultrasound probes described above in conjunction with FIGS. 1-5.

Referring to FIG. 8, the method includes displaying, using a display device, ultrasound images based on ultrasound data (block 801). In some embodiments, the ultrasound images are generated with an ultrasound probe.

Using the ultrasound probe, the method also includes providing power to electronics housed in one compartment of an ultrasound probe using a battery of the ultrasound probe (block 802), while housing the battery in a different compartment of the ultrasound probe (block 803), and using a probe cover to cover at least a portion of the ultrasound probe (804).

The method further includes forming a seal, using the battery holder, that isolates the electronics from the battery and an environment external to the ultrasound probe (block 805). In some embodiments, the battery holder forms the seal when attached to the probe cover. In addition, the method includes controlling, using the electronics, the generation of the ultrasound data (block 806).

In some embodiments, the battery holder includes a removable end cap implemented to provide service for the battery without breaking the seal. In some embodiments, the battery holder, when the end cap is attached to the battery holder, encloses the battery in the second compartment and seals the second compartment from an environment external to the ultrasound probe. In some embodiments, the battery holder and probe cover seal the first compartment from the environment external to the ultrasound probe. In some embodiments, the battery holder is implemented to transfer heat away from the electronics and towards a distal end of the ultrasound probe. In some embodiments, the probe cover includes a region for an operator grip and the battery holder is implemented to direct heat away from the region of the probe cover. In some embodiments, the ultrasound probe and the display device are communicatively coupled via a wireless communication link.

Figure 9:
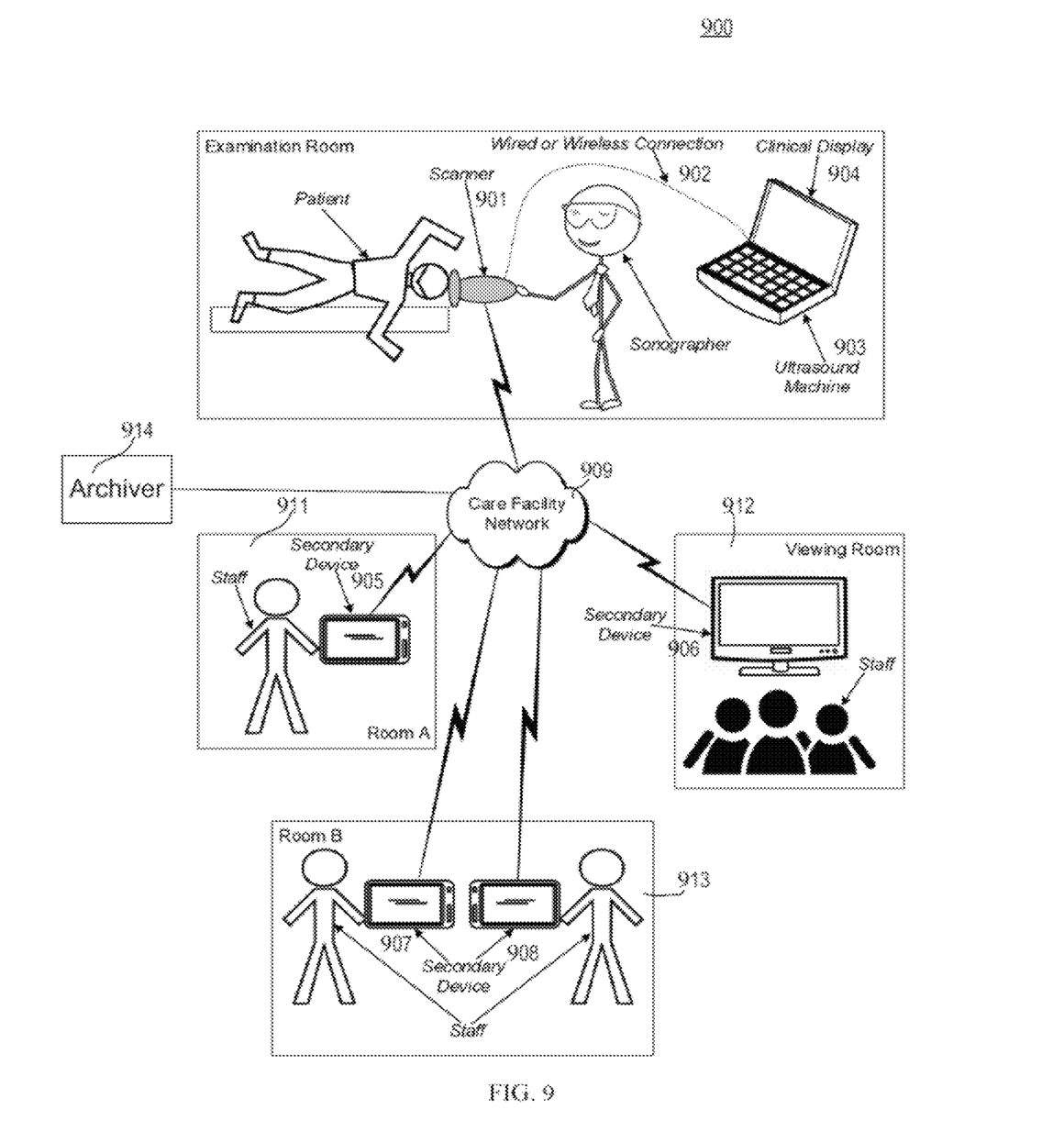
FIG. 9 illustrates an environment of an ultrasound system according to some embodiments.

FIG. 9 is a view 900 illustrating an environment of an ultrasound system according to some embodiments. As shown in FIG. 9, the ultrasound system includes a primary device that includes an ultrasound scanner 901, an ultrasound machine 903, and a clinical display 904 and one or more secondary devices, e.g., secondary devices 905, 906, 907 and 908, collectively, 905-908. In some embodiments, scanner 901 includes an ultrasound probe with a transducer array of transducer elements. In some embodiments, ultrasound machine 903 includes an ultrasound control subsystem having one or more processors. At least one processor causes electrical currents to be sent to the transducer(s) of the ultrasound probe to emit sound waves and also receives the electrical pulses from the probe that were created from the returning echoes. A processor processes the raw data associated with the received electrical pulses and forms an image that is sent to an ultrasound imaging subsystem, which displays the image on the display screen. Thus, the display screen displays ultrasound images from the ultrasound data processed by the processor of ultrasound control subsystem. In one embodiment, the ultrasound machine 903 also has one or more user input devices (e.g., a keyboard, a cursor control device, etc.) that inputs data and allows the taking of measurements from the display of the ultrasound display subsystem, a disk storage device (e.g., hard, floppy, compact disks (CD), digital video discs (DVDs)) for storing the acquired images, and a printer that prints the image from the displayed data. These devices also have not been shown in FIG. 9 to avoid obscuring the techniques disclosed herein.

In some embodiments, each of the scanner 901, ultrasound machine 903 and clinical display 904 is a portable device. In some embodiments, ultrasound machine 903 is a smart phone, tablet, or other portable device that includes a processor and a memory coupled to the processor to perform methods described herein. In some embodiments, clinical display 904 is a display on the smart phone or tablet.

Scanner 901 can be operated by a sonographer in an examination room (e.g., in an emergency department of the care facility), and can be connected to the ultrasound machine and/or clinical display in the examination room via a wireless connection 902. In some embodiments, the scanner 901 wirelessly communicates with the one or more secondary devices. That is, the scanner 901 wirelessly communicates with the one or more secondary devices 905-908, so that users can look at the same video stream on their corresponding secondary devices. In some embodiments, the scanner 901 communicates with the one or more secondary devices 905-908 and an archiver 914 in a network 909, e.g., using a multicast data transfer with Wi-Fi. In some embodiments, the archiver 914 includes a server that is connected to network 909. In some embodiments, the archiver 914 includes a processor coupled to a memory to receive ultrasound data from the scanner 901 over network 909. In some embodiments, the network 909 is a local area network, an ad-hoc network, or other network. In some embodiments, the scanner 901 transmits data to the one or more secondary devices 905-908 using a multicast IP address. In some embodiments, the communication between the scanner 901 and the one or more secondary devices 905-908 is a bidirectional communication.

The secondary devices can be operated in the same care facility or a different facility as the sonographer who operates the scanner, ultrasound machine, and clinical display. As shown in FIG. 9, a secondary device 905 is in a room A 911, a secondary device 906 is in a viewing room 912 and secondary devices 907 and 908 are in a room B 913. In some embodiments, the secondary device includes a smart phone, tablet, or other portable device that includes a processor and a memory coupled to the processor to perform methods described herein. In some embodiments, a display of the secondary device is a display on the smart phone, or a wearable heads-up device, such as, for example, a Google™ Glass.

Individuals may simultaneously and in real-time during the ultrasound examination operate the secondary devices to perform duties usually dedicated to the sonographer, such as saving images, annotating images, performing measurements, running artificial intelligence (AI) routines, archiving, and the like, thus offloading the responsibilities of the sonographer and allowing the sonographer to concentrate on the patient. Further, these individuals can provide instructions/insights to the sonographer. The secondary devices can use the same archiving mechanism as the ultrasound machine, and/or a distinctly separate set of archivers including archiver 914. For more information on the ultrasound system environment of FIG. 9, see U.S. patent application Ser. No. 17/830,060, entitled "Ultrasound System for a Virtual Sonography Team," filed Jun. 1, 2022, and incorporated herein by reference.

All of the methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions, or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid-state memory chips or magnetic disks, into a different state. In some embodiments, the computer system may be a cloud-based computing system whose processing resources are shared by multiple distinct business entities or other users.

Depending on the embodiment, certain acts, events, or functions of any of the processes or algorithms described herein can be performed in a different sequence, can be added, merged, or left out altogether (e.g., not all described operations or events may be necessary for the practice of the algorithm). Moreover, in some embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware (e.g., ASICs or FPGA devices), computer software that runs on computer hardware, or combinations of both. Moreover, the various illustrative logical blocks and modules described in connection with the embodiments disclosed herein can be implemented or performed by a machine, such as a processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements or steps. Thus, such conditional language is not generally intended to imply that features, elements or steps are in any way required for one or more embodiments or that one or more embodiments necessarily include logic for deciding, with or without other input or prompting, whether these features, elements or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, or Z). Thus, such disjunctive language is not generally intended to, and should not, imply that certain embodiments require at least one of X, at least one of Y, and at least one of Z to each be present.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

What is claimed is:

1. An ultrasound probe comprising:
   electronics configured to control transmission and reception of ultrasound signals;
   a battery configured to provide power to the electronics;
   a battery holder configured to house the battery and having an elongated portion upon which the electronics are coupled, the battery holder to transfer heat away from the electronics; and
   an enclosure configured to establish a seal that isolates the electronics from the battery and an environment external to the ultrasound probe.

2. The ultrasound probe as described in claim 1, wherein the battery holder and the enclosure are implemented to allow service of the battery without breaking the seal.

3. The ultrasound probe as described in claim 2, wherein the service of the battery includes replacement of the battery.

4. The ultrasound probe as described in claim 2, further comprising an end cap removably coupled to the battery holder to implement the service of the battery.

5. The ultrasound probe as described in claim 4, wherein the battery holder is implemented to transfer the heat away from the electronics and towards the end cap.

6. The ultrasound probe as described in claim 4, further comprising an additional battery implemented to provide at least one of additional power to the electronics and charging current to the battery, wherein the end cap includes at least one connector implemented to receive the at least one of the additional power and the charging current from the additional battery, wherein the additional battery is implemented to be removably attached to the end cap.

7. The ultrasound probe as described in claim 6, wherein the additional battery is housed in a material having a first thermal conductivity in a first direction and a second thermal conductivity in a second direction.

8. The ultrasound probe as described in claim 1, wherein the battery holder comprises a material having a first thermal conductivity in a first direction and a second thermal conductivity in a second direction.

9. The ultrasound probe as described in claim 1, wherein the electronics are mounted to a printed circuit board that is attached to the battery holder.

10. The ultrasound probe as described in claim 1, wherein the battery is insertable into and removable from the battery holder.

11. An ultrasound system comprising:
a display device configured to display ultrasound images based on ultrasound data; and
an ultrasound probe communicatively coupled to the display device and configured to generate the ultrasound data, the ultrasound probe including:
electronics housed in a first compartment of the ultrasound probe and configured to control the generation of the ultrasound data;
a battery housed in a second compartment of the ultrasound probe and configured to provide power to the electronics;
a probe cover; and
a battery holder that when attached to the probe cover forms a seal that isolates the first compartment from the second compartment, the electronics being coupled upon an elongated portion of the battery holder, and wherein the battery holder is implemented to transfer heat away from the electronics and towards a distal end of the ultrasound probe.

12. The ultrasound system as described in claim 11, wherein the battery holder includes a removable end cap implemented to provide service for the battery without breaking the seal.

13. The ultrasound system as described in claim 12, wherein the battery holder is implemented to, when the end cap is attached to the battery holder, enclose the battery in the second compartment and seal the second compartment from an environment external to the ultrasound probe.

14. The ultrasound system as described in claim 13, wherein the battery holder and probe cover are implemented to seal the first compartment from the environment external to the ultrasound probe.

15. The ultrasound system as described in claim 11, wherein the probe cover includes a region for an operator grip and the battery holder is implemented to direct heat away from the region of the probe cover.

16. The ultrasound system as described in claim 11, wherein the ultrasound probe and the display device are communicatively coupled via a wireless communication link.

17. A method of manufacturing an ultrasound probe, the method comprising:
forming a battery holder configured to house a battery in a first compartment of the battery holder;
mounting electronics upon an elongated portion of the battery holder outside of the first compartment, the electronics configured to control transmission and reception of ultrasound signals;
sealing a probe cover to the battery holder, the sealing creating a second compartment inside the ultrasound probe that houses the electronics and that is isolated from the first compartment and an environment external to the ultrasound probe; and
inserting a battery into the first compartment of the battery holder after sealing the probe cover to the battery holder.

18. The method as described in claim 17, further comprising:
attaching an end cap to the battery holder to seal the first compartment and the battery from the environment external to the ultrasound probe.

19. The method as described in claim 17, further comprising placing a bonding agent between the probe cover and the battery holder, wherein the sealing includes curing the bonding agent with the battery removed from the ultrasound probe.

* * * * *